US00PP10229P

United States Patent [19]

Zary

[11] Patent Number: Plant 10,229

[45] Date of Patent: Feb. 10, 1998

[54] SHRUB ROSE PLANT NAMED 'JACAIR'

[75] Inventor: Keith W. Zary, Thousand Oaks, Calif.

[73] Assignee: Bear Creek Gardens, Inc., Medford, Oreg.

[21] Appl. No.: 764,731

[22] Filed: Dec. 3, 1996

[51] Int. Cl.[6] ..... A01H 5/00

[52] U.S. Cl. ..... Plt./1

[58] Field of Search ..... Plt./1, 22, 7.1

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the shrub class having bright, dark pink-red flowers that are presented in large clusters; a compact, spreading, arching growth habit; small, dark green, glossy, leathery foliage; ease of propagation from softwood cuttings; and resistance to powdery mildew and rust.

1 Drawing Sheet

The present invention relates to a new and distinct variety of rose plant of the shrub class which was originated by me by crossing the variety The Fairy (unpatented) with an unnamed seedling.

The primary objective of this breeding was to produce a new rose variety having the attractive, low-growing, arching, compact habit, hardiness and plant health of the female parent combined with the dark pink flower color and white eye marking of the male parent. The objective was substantially achieved, along with other desirable improvements, as evidenced by the following unique combination of characteristics that are outstanding in the new variety and that distinguish it from its parents, as well as from all other varieties of which I am aware:

1. A spreading, arching, but quite compact growth habit;
2. Ease of propagation from softwood cuttings;
3. Small, glossy, dark green, leathery foliage;
4. Attractive, dark pink-red blooms presented in large clusters; and
5. Resistance to rust and powdery mildew.

Asexual reproduction of this new variety by softwood cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—The Fairy.

*Pollen parent.*—An unnamed seedling.

Classification:

*Botanical.*—*Rosa hybrida.*

*Commercial.*—Shrub.

FLOWER

Observations made from specimens grown from January to September, 1996 in a garden environment at Somis, Calif.

Blooming habit: Continuous.

Bud:

*Size.*—½ inch long when the petals start to unfurl.

*Form.*—The bud form is short, pointed ovoid.

*Color.*—When sepals first divide, the top of the bud is Red Group 53D while the base of the petals is Yellow Group 2D. When half blown, the upper sides of the petals are Red Group 53D, with White Group 155D near the base of the petals; and the lower sides of the petals are Red Group 54D on the upper portion, with White Group 155D near the base.

*Sepals.*—Color: Green Group 138C. Surface texture: Covered in fine hairs. There are three lightly appendaged sepals. There are two unappendaged sepals with hairy edges.

*Receptacle.*—Color: Green Group 138B. Shape: Apple. Size: Small (⅛ inch×⅛ inch). Surface: Smooth.

*Peduncle.*—Length: Short (½ inch to ¾ inch). Surface: Glandular. Color: Light green and sometimes bronzy if exposed to intense sunlight. Strength: Stiff, erect, slender.

Bloom:

*Size.*—Small. Average open size is 1 to 1¼ inches.

*Borne.*—Several together and in clusters. If in clusters: Flat, near corymb in shape, with up to 20 flowers.

*Stems:*—Short, strong. Average length is about 6 to 8 inches.

*Form.*—When first open: Flat. Permanence: Retains its form to the end.

*Petalage.*—Number of petals under normal conditions: 10 to 15.

*Color.*—The upper side of the petals is Red Group 53D except near petal base, where it is White Group 155D. The reverse side of the petals is Red Group 54D except near petal base, where it is White Group 155D. The base of each petal has a small (1/16 inch×1/16 inch) Yellow Group 2D half moon at the point of attachment. The major color on the upper side is Red Group 53D.

*Variegations.*—Each petal has some white variegation, which is most pronounced on the innermost petals.

*Discoloration.*—The general tonality at the end of the first day: No change. At the end of the third day: General slow fade to Red Group 54D. No change on the petal reverse.

*Fragrance.*—Slight.

Petals:

*Texture.*—Thick.

*Shape.*—Deltoid.

*Form.*—Flat.

*Arrangement.*—Imbricated, with few petaloids in the center.

*Persistence.*—Drop off cleanly.

*Lastingness.*—On the plant: Short (3 to 4 days). As a cut flower: (Not tested).

Reproductive parts:

*Anthers.*—Size: Small. Quantity: Many. Color: Yellow. Arrangement: Regular around styles.

*Filaments.*—Color:Yellow.

*Pollen.*—Color: Gold yellow.

*Styles.*—Color: Red.

*Stigmas.*—Color: Greenish white.

Form: Shrub.

Growth: Vigorous, compact, arching and spreading. At one year, on its own roots, a plant grown in Southern California with spread 3 feet and be about 18 inches to 24 inches tall.

Foliage: Number of leaflets on normal mid-stem leaves: 7.

*Size.*—2 to 2½ inches×1½ inches.

*Quantity.*—Abundant.

*Color.*—New foliage: Very briefly greyed Red Group 180A on both surfaces. Old foliage: Upper surface Green Group 137A. Lower surface Green Group 139C.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Rough, with prickles.

*Stipules.*—Medium (¼ inch), serrated, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅛ inch), straight to hooked slightly downward.

*Color when young.*—Red.

Small prickles:

*Quantity.*—On main stalks: None. On laterals: Many.

*Color.*—Red.

I claim:

1. A new and distinct variety of rose plant of the shrub class, substantially as herein shown and described, characterized particularly as to novelty by the unique combination of its bright dark pink-red flowers that are presented in large clusters; its compact, spreading, arching growth habit; its small, dark green, glossy, leathery foliage; its ease of propagation from softwood cuttings; and its resistance to powdery mildew and rust.

* * * * *

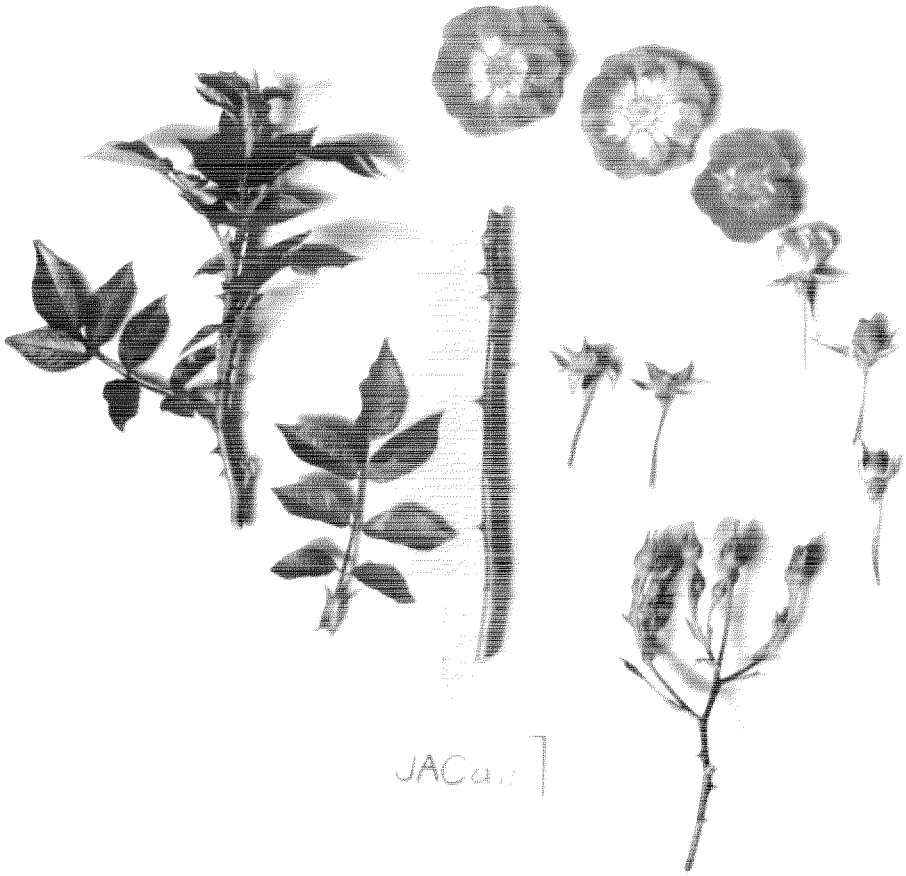
JACa